(12) United States Patent
Chuang et al.

(10) Patent No.: US 9,284,528 B2
(45) Date of Patent: *Mar. 15, 2016

(54) USE OF STEM CELL CONDITIONED MEDIUM TO INHIBIT OXIDATION FOR ANTI-AGING SKIN

(71) Applicant: GROWGENE BIOTECH INC., Taipei (TW)

(72) Inventors: Pei-Chuan Chuang, Taipei (TW); Huei-Chun Liu, Taipei (TW)

(73) Assignee: Growgene Biotech Inc., Taipei (TW)

( * ) Notice: Subject to any disclaimer, the term of this patent is extended or adjusted under 35 U.S.C. 154(b) by 34 days.

This patent is subject to a terminal disclaimer.

(21) Appl. No.: 14/256,147

(22) Filed: Apr. 18, 2014

(65) Prior Publication Data

US 2015/0299650 A1    Oct. 22, 2015

(51) Int. Cl.
| | | |
|---|---|---|
| *A61K 35/50* | (2015.01) | |
| *A61K 35/12* | (2015.01) | |
| *C12N 5/00* | (2006.01) | |
| *A61K 8/98* | (2006.01) | |
| *A61Q 19/08* | (2006.01) | |

(52) U.S. Cl.
CPC ............. *C12N 5/0018* (2013.01); *A61K 8/981* (2013.01); *A61Q 19/08* (2013.01); *C12N 2501/115* (2013.01); *C12N 2502/025* (2013.01)

(58) Field of Classification Search
None
See application file for complete search history.

(56) References Cited

U.S. PATENT DOCUMENTS

| | | | | |
|---|---|---|---|---|
| 2008/0311093 | A1* | 12/2008 | Skinner ..................... | 424/93.21 |
| 2009/0136459 | A1* | 5/2009 | Wu et al. ..................... | 424/93.7 |
| 2010/0143289 | A1* | 6/2010 | Cohen et al. ................. | 424/85.1 |
| 2010/0323027 | A1* | 12/2010 | Lim et al. ..................... | 424/520 |
| 2011/0003008 | A1 | 1/2011 | Lim | |
| 2011/0294731 | A1* | 12/2011 | Torfi .............................. | 514/7.6 |
| 2012/0141399 | A1* | 6/2012 | You et al. ........................ | 424/62 |
| 2012/0230940 | A1 | 9/2012 | Naughton et al. | |
| 2014/0148915 | A1* | 5/2014 | Aljitawi et al. ............ | 623/23.72 |

FOREIGN PATENT DOCUMENTS

| | | |
|---|---|---|
| CN | 1376067 A | 10/2002 |
| CN | 102014934 A | 4/2011 |
| TW | 201338810 A | 10/2013 |

OTHER PUBLICATIONS

Arno et al. Stem Cell Research & Therapy 2014, 5:28, pp. 1-13.*

\* cited by examiner

*Primary Examiner* — Chris R Tate
*Assistant Examiner* — Douglas F White
(74) *Attorney, Agent, or Firm* — Rosenberg, Klein & Lee

(57) ABSTRACT

A use of a stem cell conditioned medium to inhibit oxidation for anti-aging skin. First, mesenchymal stem cells are cultured in a cell culture dish containing a complete growth medium. After mesenchymal stem cells are sub-cultured in the complete growth media for three times and transferred to a basal medium, a conditioned medium can be acquired from the basal medium.

2 Claims, 5 Drawing Sheets

A

B

USE OF STEM CELL CONDITIONED MEDIUM TO INHIBIT OXIDATION FOR ANTI-AGING SKIN

BACKGROUND OF THE INVENTION

1. Field of the Invention

The present invention relates to a use of a stem cell conditioned medium to inhibit oxidation for anti-aging skin. The conditioned medium acquired from WJMSCs conditioned basal medium can effectively scavenge free radicals and increase the survival rate of skin cells under oxidative stress, so that it can improve users undesired skin conditions, e.g. oxidation and aging.

2. Description of Related Art

Nowadays, people become exposed to more intense ultraviolet (UV) radiation than before due to the ozone hole. UV radiation is one of the primary factors contributing to the oxidation of the skin, which causes rapid oxidation and aging of cells. Moreover, the ability to scavenge free radicals is known to gradually decrease with people's ages. If people don't timely care their skin after UV radiation, cell damage will become increasingly severe. Therefore, in order to maintain or restore youthful and flawless appearance, not only females but also males have paid much attention to skin care.

Currently, various natural substances are identified to have antioxidant effects, including vitamin C (L-ascorbic acid), vitamin E, β-carotene, kojic acid, super dismutase and the like. However, some limitations and side effects are existed, e.g. vitamin C is easily oxidized in the sun or in contact with air, cannot withstand high temperature, and may cause skin irritation and redness when the concentration is greater than 5%; and kojic acid is also susceptible to oxidation, leading to discoloration and skin allergy, and may cause cytotoxicity and lesions after a long-term excessive use. Moreover, some antioxidant agents applied on users' skin may directly damage skin cells, which also cause cytotoxicity. Therefore, it is necessary to develop a safer and more effective antioxidant ingredient.

In these years, studies of stem cells have been a growing trend in the world. Stem cells can mainly be divided into two categories, embryonic stem cells and adult stem cells. Mesenchymal stem cells (MSCs) belong to adult stem cells and have a great potential for differentiation. MSCs can differentiate into not only tissues (such as skeleton) derived from mesoderm, but also visceral cells (such as liver and pancreas) derived from endoderm and neurons derived from ectoderm. MSCs are ubiquitous in adults' bodies and can be isolated from bone marrows and various organs. However, the number of MSCs in the bodies is small, and adults' MSCs are known to gradually decrease with the age of the donors. Therefore, how to obtain a sufficient amount of MSCs becomes very important. Bone marrow MSCs are mainly derived from adult bone marrow, but invasive ways to get the bone marrow MSCs may cause pain and discomfort to donors. Umbilical cords contain a number of rich and young MSCs with strong differentiation potential, so they can be used as an important source of mesenchymal stem cells. In comparison with obtaining MSCs from bone marrows, obtaining MSCs from umbilical cords is relatively easy. Moreover, recent studies showed that mesenchymal stem cell-conditioned medium (MSC-CM) can increase the survival rate of dorsal root ganglia cells under oxidative stress of hydrogen peroxide and presents neuroprotective properties (*PLoS One.* 8(5):e62807, 2013).

SUMMARY OF THE INVENTION

In view of the above-mentioned problems, the object of the present invention is to provide a use of a stem cell conditioned medium to inhibit oxidation for anti-aging skin. The conditioned medium acquired from WJMSCs conditioned basal medium can effectively scavenge free radicals and increase the survival rate of skin cells under oxidative stress. Accordingly, cosmetic composition containing the conditioned medium can be used to improve users' undesired skin conditions, so as to achieve efficacy of anti-oxidation and anti-aging.

Disclosed herein is a use of a stem cell conditioned medium to inhibit oxidation for anti-aging skin, wherein the stem cell conditioned medium is made by the steps of (a) culturing stem cells in a cell culture dish containing a complete growth medium, wherein the complete growth medium includes α-MEM, fetal bovine serum, and human-basic fibroblast growth factors; and (b) sub-culturing the stem cells for at least three times (preferably for three times) in the complete growth medium and transferring the stem cells to a basal medium for acquiring the stem cell conditioned medium, wherein the basal medium includes α-MEM and human-basic fibroblast growth factors (without fetal bovine serum).

Disclosed herein is another use of a stem cell conditioned medium to decrease oxidation, wherein more than or equal to 10 wt. % of the stem cell conditioned medium is applied to a skin for scavenging free radicals and increasing the survival rate of skin cells under oxidative stress.

According to an embodiment of the present invention, the stem cell is mesenchymal stem cell, preferably human Wharton's jelly-derived mesenchymal stem cell.

According to an embodiment of the present invention, the complete growth medium includes about 10 wt. %~20 wt. % of fetal bovine serum, about 2~6 ng/ml of human-basic fibroblast growth factors, and a remaining weight percentage of minimum essential medium alpha (α-MEM).

According to an embodiment of the present invention, the basal medium includes about 2~6 ng/ml of human-basic fibroblast growth factors and a remaining weight percentage of minimum essential medium alpha (α-MEM).

DETAILED DESCRIPTION OF THE PREFERRED EMBODIMENT

Figure 1:
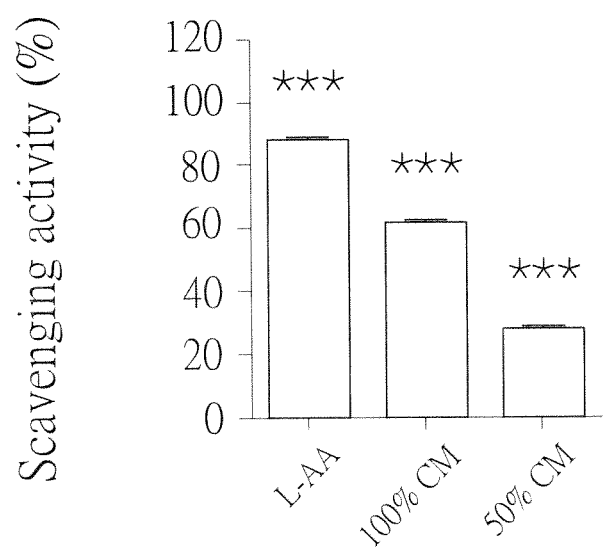
FIG. 1 is a diagram showing that WJMSC-CM effectively scavenges $H_2O_2$.

Disclosed herein is a use of a stem cell conditioned medium to inhibit oxidation for anti-aging skin, wherein the stem cell conditioned medium is manufactured by the steps of (a) culturing stem cells in a cell culture dish containing a complete growth medium, wherein the complete growth medium includes about 10 wt. %~20 wt. % (preferably 20 wt. %) of fetal bovine serum, about 2~6 ng/ml (preferably 4 ng/ml) of human-basic fibroblast growth factors, and a remaining weight percentage of minimum essential medium alpha (α-MEM); and (b) sub-culturing the stem cells for at least three times (preferably for three times) in the complete growth medium and transferring the stem cells to a basal medium for acquiring the stem cell conditioned medium, wherein the basal medium includes about 2~6 ng/ml (preferably 4 ng/ml) of human-basic fibroblast growth factors and a remaining weight percentage of α-MEM (but without fetal bovine serum), and wherein the stem cell is mesenchymal stem cell, preferably human Wharton's jelly-derived mesenchymal stem cell.

Disclosed herein is another use of a stem cell conditioned medium to decrease oxidation, wherein at least 10 wt. % of the stem cell conditioned medium is applied to a skin for scavenging free radicals and increasing the survival rate of skin cells under oxidative stress, wherein the stem cell conditioned medium is manufactured by the steps of (a) culturing stem cells in a cell culture dish containing a complete growth medium, wherein the complete growth medium includes α-MEM, fetal bovine serum, and human-basic fibroblast growth factors; and (b) sub-culturing the stem cells for at least three times (preferably for three times) in a basal medium for acquiring the stem cell conditioned medium, wherein the basal medium includes about 2~6 ng/ml (preferably 4 ng/ml) of human-basic fibroblast growth factors and a remaining weight percentage of α-MEM.

Hereinafter, an exemplary embodiment of the present invention will be described in detail with reference to the accompanying drawings.

Example 1

Analyze the Effect of Stem Cell Conditioned Medium on Scavenges $H_2O_2$

Cell Culture

Human foreskin fibroblasts (Hs68: BCRC 603800) were cultured in dishes containing complete growth medium (BD Falcon/BD biosciences) which includes Dulbecco's Modified Eagle Medium (DMEM) (Gibco) supplemented with 10% fetal bovine serum (FBS) (Gibco). Human Wharton's jelly-derived mesenchymal stem cells (WJMSC: BCRC H-WJ001) were cultured in dishes containing complete growth medium (BD Falcon/BD biosciences) which includes DMEM supplemented with 20% FBS and 4 ng/ml human-basic fibroblast growth factor (bFGF) (Peprotech). The Hs68 and the WJMSCs were incubated at 37° C. in 5% $CO_2$, and were sub-cultured after incubation for three days.

In the subculture (cell passaging) experiment, the culture medium (complete growth medium) was removed and the attached cells were rinsed by phosphate buffered saline (PBS) (Roche). After the supernatant was removed, cells were incubated in 0.05% trypsin-EDTA (Life Technologies) for 5 minutes, and then the detached cells can be acquired from the dishes. The cells were resuspended in culture medium and centrifuged at 1,200 rpm for 3 minutes. After the supernatant was removed, cell pellets were resuspended in culture medium and cultured at 37° C. in 5% $CO_2$. Then cells were sub-cultured for three times in the complete growth media.

Preparation of Conditioned Medium

Human Wharton's jelly-derived mesenchymal stem cells (WJMSCs) were seeded onto culture dishes at a cell density of $5\times10^4$ cells/cm$^2$ and were incubated for one day. Then the attached cells were washed three times with PBS, and the medium was replaced with basal medium (containing DMEM and 4 ng/ml bFGF). After WJMSCs were maintained for an additional 48 hours, the basal medium were collected into a 50-ml centrifuge tube and centrifuged at 2,000 rpm for 10 minutes. Then the supernatant was filtered through a 0.22 μm filtration unit (BD Falcon/BD biosciences) and used as WJMSC conditioned medium (WJMSC-CM). The WJMSC-CM was stored at −20° C.

Hydrogen peroxide ($H_2O_2$) Scavenging Assay

The hydrogen peroxide scavenging assay was carried out following the procedure of Ruch et al. (1989). For this aim, a solution of 2 mg/L $H_2O_2$ was prepared in phosphate-buffered saline (PBS) (pH7.4). Each of samples including 1 ml of 100% conditioned medium, 50% conditioned medium, or 200 mg/L L-ascorbic acid (L-AA) was added to 0.6 mL of $H_2O_2$ solution for 10-minute reaction. The absorbance value of the reaction mixture was recorded at 230 nm. Scavenging effects (%)=[($A_{230}$ of control−$A_{230}$ of sample)/($A_{230}$ of control)]=100%. The experiments were performed in triplicate. Results were expressed as mean±SEM. *** P<0.005.

Example 2

Analyze the Effect of Stem Cell Conditioned Medium on Scavenges ABTS Free Radicals ABTS Free Radicals Scavenging Assay An antioxidant assay kit (Cayman) was used for this assay according to the instructions. Each of samples including 10 μl of 6.25%~100% conditioned medium or 0.0625~1 mM L-ascorbic acid (L-AA) was mixed with 10 μl of metmyoglobin, 150 μl chromogen, and 40 μl hydrogen peroxide for reaction at room temperature for 5 minutes. Because stem cell conditioned medium (CM) is a composite component, a percentage (%) instead of a concentration (mM) is presented as the unit of CM herein. The absorbance value of the reaction mixture was recorded at 750 nm.

Example 3

Analyze the Effect of Stem Cell Conditioned Medium on Scavenges DPPG Free Radicals DPPH Free Radicals Scavenging Assay Each of samples including 1 ml of 1%~100% conditioned medium was mixed with 1 ml of 95% EtOH containing 0.1 mM DPPH for reaction at room temperature for 30 minutes. The absorbance value of the reaction mixture was recorded at 517 nm. The experiments were performed in triplicate. Results were expressed as mean±SEM. *P<0.05; *** P<0.005.

Example 4

Analyze the Survival Rate of Skin Cells under Oxidative Stress

Cell Antioxidant Activity Determination

Human foreskin fibroblasts (Hs68) were seeded onto 6-well dishes at a cell density of $2\times10^4$ cells/cm$^2$ and were incubated for one day. Then the original medium was removed and the cells were incubating in a medium containing the basal medium (only containing DMEM), stem cell conditioned medium (CM), and 0~0.025 mM $H_2O_2$ for 24 hours. Three fields from each well were measured by an optical microscope (Leica). Then the attached cells were washed three times with PBS. The supernatant were removed and cells were trypsinized with 0.05% trypsin-EDTA (Life Technologies) at 37° C. for 5 minutes. Cells were resuspend in a culture medium and centrifuged at 1,200 rpm for 3 min. After the supernatant were removed, the remaining cell pellets were resuspend in 0.2 ml PBS and added with 0.2 ml trypan blue (Invitrogen) (PBS: trypan blue=1:1) for staining. Trypan blue exclusion test and hemocytometer were used to calculate the number of cells. The experiments were performed in triplicate.

Result

Result 1: Stem Cell Conditioned Medium can Effectively Scavenges $H_2O_2$

Referring to FIG. 1A, it is a diagram showing that WJMSC-CM effectively scavenges $H_2O_2$. The results of scavenging activity indicated that 200 mg/L L-ascorbic acid (L-AA), 100% CM and 50% CM can respectively scavenge 88.18%±1.06%, 61.69%±1.88% and 27.77%±1.32% of $H_2O_2$ by student's t-test analysis. The scavenging activity of sterile water plus hydrogen peroxide treatment is defined as 100% herein. The experiments were performed in triplicate. Results were expressed as mean±SEM. *** $P<0.005$. It can be learned from the result that the stem cell conditioned medium can effectively scavenge $H_2O_2$.

Figure 2A:
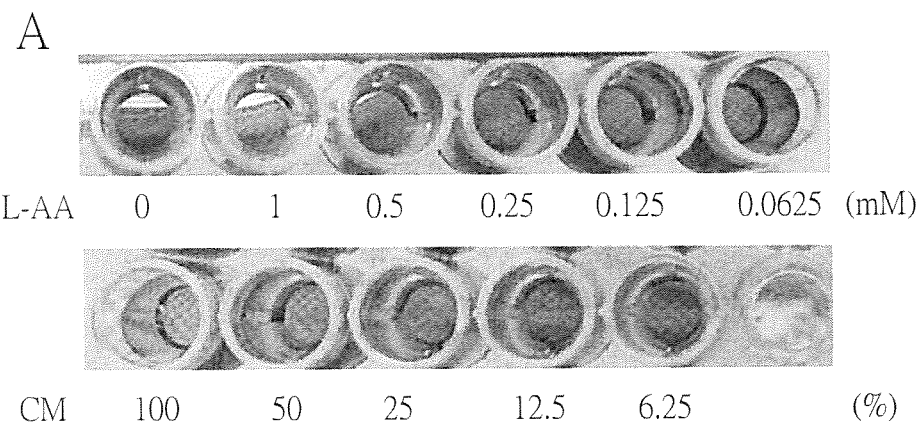
FIG. 2A is a representative diagram showing the effect of WJMSC-CM on scavenging ABTS free radicals.
Figure 2B:
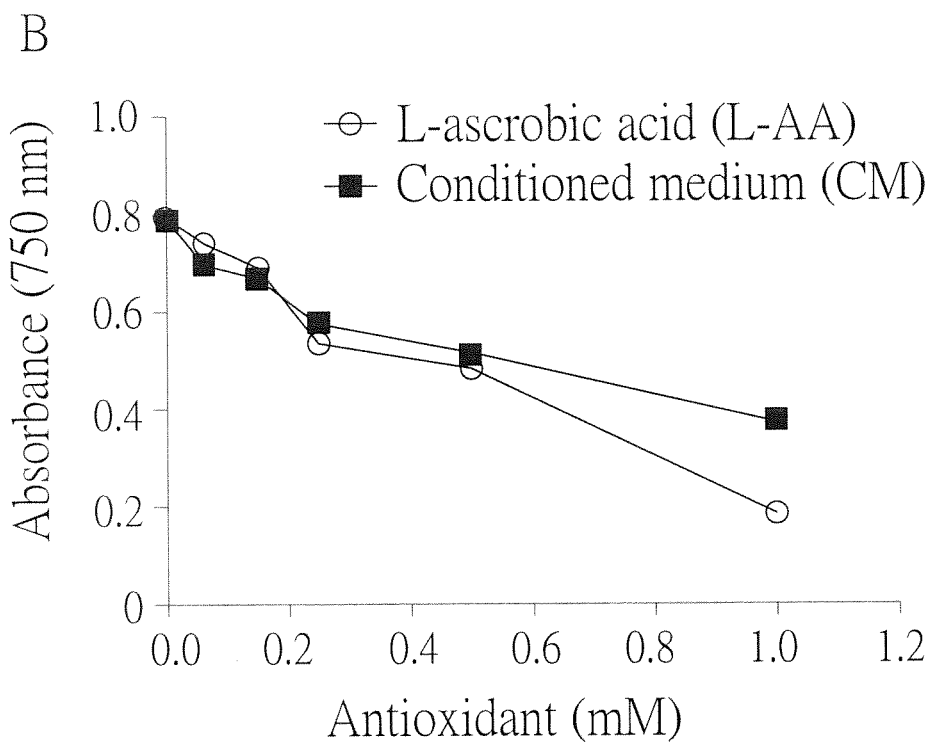
FIG. 2B is a diagram showing that WJMSC-CM effectively scavenges ABTS free radicals.

Result 2: Stem Cell Conditioned Medium can Effectively Scavenge ABTS Free Radicals Referring to FIG. 2A, it is a representative diagram showing the effect of WJMSC-CM on scavenging ABTS free radicals. Various concentration of L-ascorbic acid (L-AA) or stem cell conditioned medium (CM) was mixed with an appropriate amount of ABTS and oxidants for reaction. ABTS has an absorption peak at 750 nm. This assay is based on the ability of antioxidants to reduce ABTS into its colourless form and the extent of decolourisation corresponding to the absorbance reduction of ABTS. FIG. 2B is a diagram showing that WJMSC-CM effectively scavenges ABTS free radicals. It can be learned from the statistical analysis that $IC_{50}$ of L-ascorbic acid (L-AA) is 0.8059 mM, equivalent to the antioxidant ability of 119.45% of stem cell conditioned medium (CM). The result indicated that stem cell conditioned medium has the ability to scavenge ABTS free radicals.

Figure 3A:
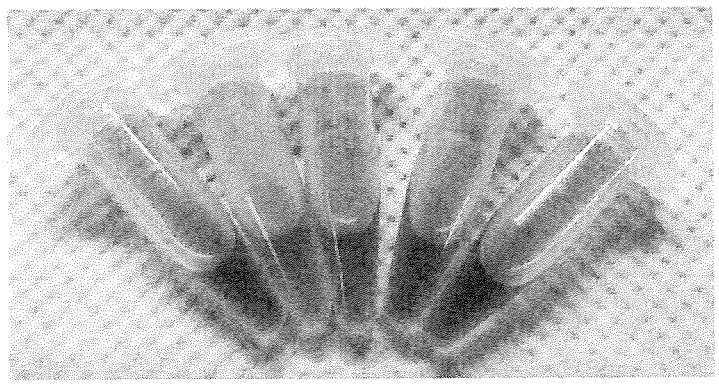
FIG. 3A is a representative diagram showing the effect of WJMSC-CM on scavenging DPPH free radicals.
Figure 3B:
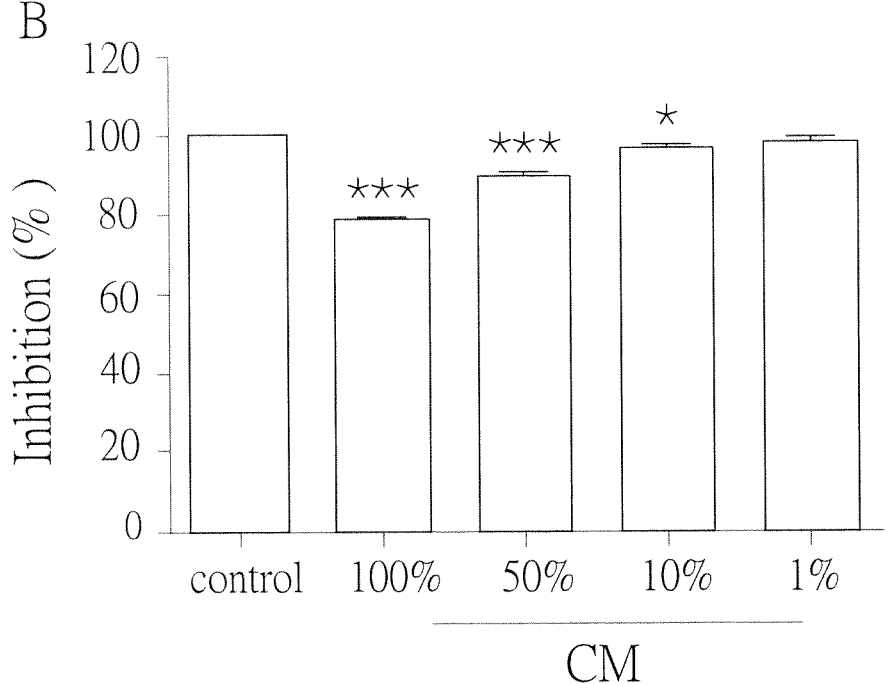
FIG. 3B is a diagram showing that WJMSC-CM effectively scavenges DPPH free radicals.

Result 3: Stem Cell Conditioned Medium can Effectively Scavenge DPPH Free Radicals Referring to FIG. 3A, it is a representative diagram showing the effect of WJMSC-CM on scavenging DPPH free radicals. Various concentration of stem cell conditioned medium (CM) was mixed with an appropriate amount of DPPH for reaction. DPPH has an absorption peak at 517 nm. A reduction of DPPH by antioxidants will change the absorbance. Therefore, antioxidant capacity can be determined by the absorbance. FIG. 3B is a diagram showing that WJMSC-CM effectively scavenges DPPH free radicals. It can be learned from the statistical analysis that more than or equal to 10% of stem cell conditioned medium (CM) has ability to decrease DPPH free radicals, which indicates stem cell conditioned medium has the ability to scavenge DPPH free radicals.

Figure 4:
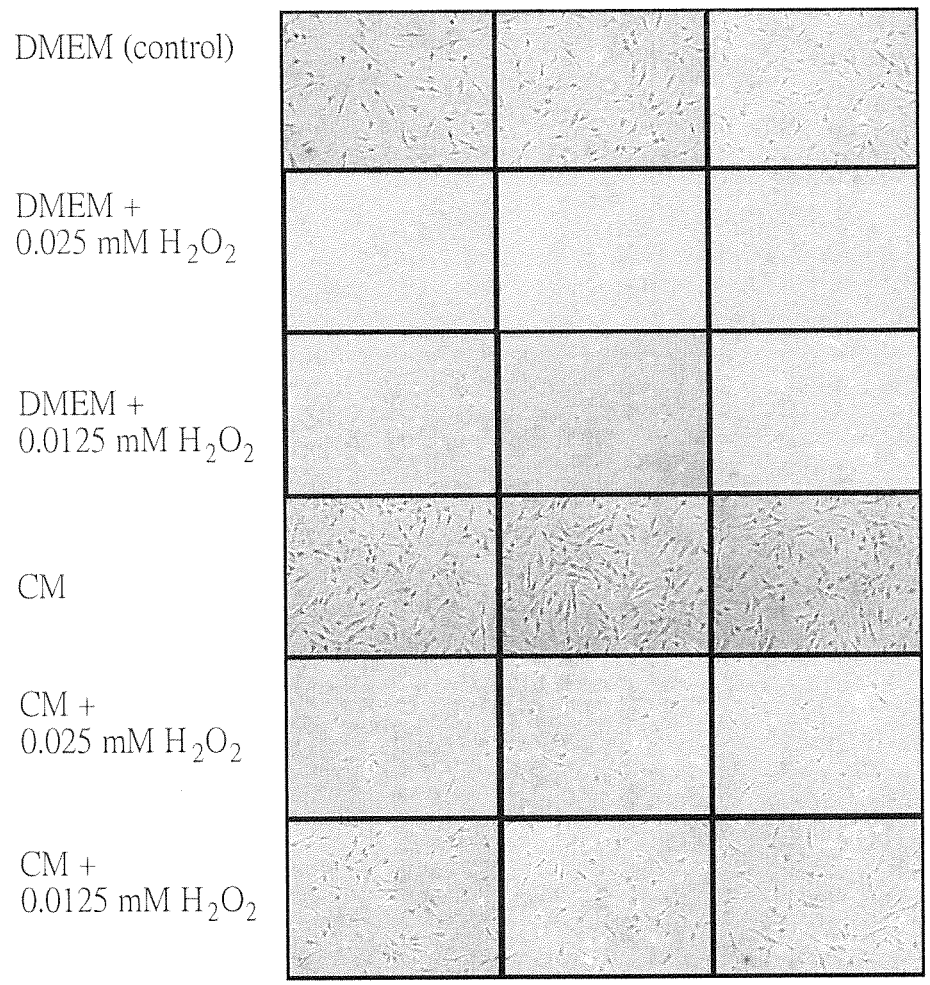
FIG. 4 is a representative diagram showing the survival rate of skin cells under oxidative stress.
Figure 5:
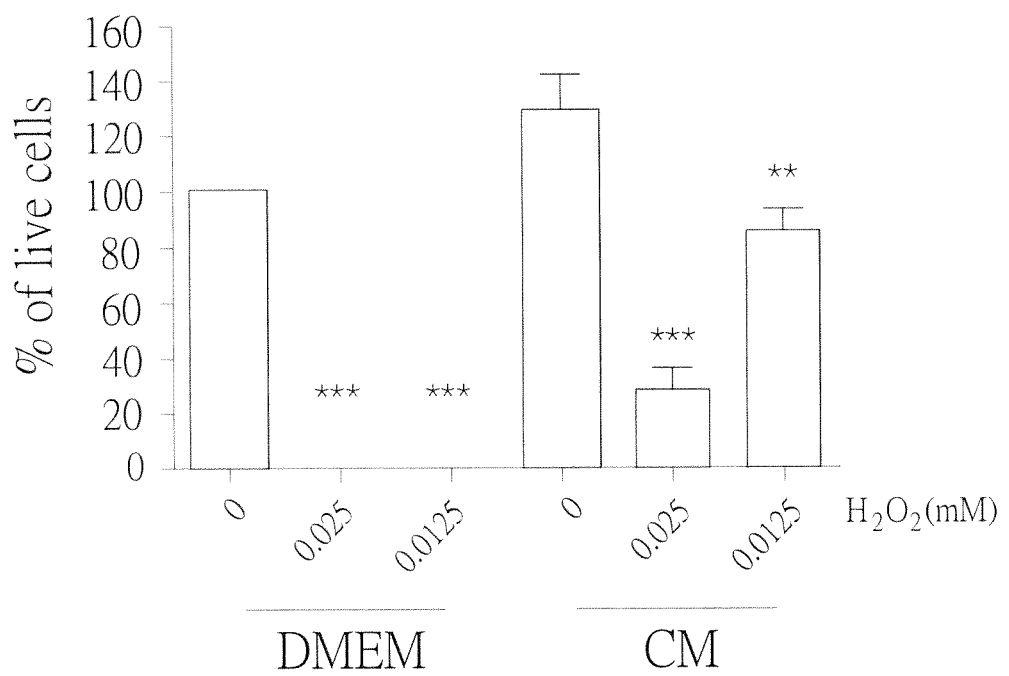
FIG. 5 is a diagram showing that WJMSC-CM increases the survival rate of skin cells under oxidative stress.

Result 4: Stem Cell Conditioned Medium can Increase the Survival Rate of Skin Cells under Oxidative Stress Referring to FIG. 4, it is a representative diagram showing the survival rate of skin cells under oxidative stress. Fibroblasts were treated with DMEM (control group), DMEM+0.025 mM $H_2O_2$, DMEM+0.0125 mM $H_2O_2$, stem cell conditioned medium (CM), CM+0.025 mM $H_2O_2$ or CM+0.0125 mM $H_2O_2$, and the result showed that stem cell conditioned medium significantly increased cell viability. FIG. 5 is a diagram showing that WJMSC-CM increases the survival rate of fibroblasts under oxidative stress. By student's t-test analysis, the results showed that all cells were dead in the groups treated with DMEM+0.025 mM $H_2O_2$ and DMEM+0.0125 mM $H_2O_2$. However, there were 28.57%±8.25% and 85.71%±8.25% cells still alive (% of live cells) in the groups treated with CM+0.025 mM $H_2O_2$ and CM+0.0125 mM $H_2O_2$, respectively. The survival rate (% of live cells) of DMEM treatment is defined as 100% herein. The experiments were performed in triplicate. Results were expressed as mean±SEM. $P<0.001$; *$P<0.005$. It can be learned from the result that the stem cell conditioned medium has antioxidant capacity since it can effectively increase the survival rate of fibroblasts under oxidative stress.

To sum up, human derived Wharton's Jelly mesenchymal stem cell (WJMSC) release a large number of growth factors to media, forming Wharton's Jelly mesenchymal stem cell conditioned media (WJMSC-CM). The WJMSC-CM can effectively scavenge $H_2O_2$, ABTS free radicals and DPPH free radicals as well as increase the survival rate of skin cells under oxidative stress. Accordingly, the WJMSC-CM can be further used as a material added to the cosmetic composition for improving users' undesired skin conditions, e.g. oxidation and aging.

According to the above description, in comparison with the traditional technique, a use of a stem cell conditioned medium to inhibit oxidation for anti-aging skin according to the present invention has the advantages as following:

1. The mesenchymal stem cell conditioned medium (WJMSC-CM) containing a large number of growth factors can effectively scavenge free radicals and increase the antioxidant ability of cell, so as to solve the problems of skin damage by UV radiation.
2. In comparison with obtaining MSCs from bone marrows, Wharton's jelly MSCs can be acquired from newborn babies' unwanted umbilical cords. Therefore, collecting MSCs from umbilical cords may not cause pain to donors and can prevent ethical problems. Moreover, the number of stem cells in umbilical cords is larger than that of other parts in human's bodies, so obtaining MSCs from umbilical cords is relatively easy.
3. In comparison with bone marrows-derived MSCs, Wharton's jelly MSCs belong to the earlier stage cells and can differentiate into much more cell types. Therefore, the conditioned media of Wharton's jelly MSCs, which contains protein factors, have a better ability to decrease oxidation for skin repair.

What is claimed is:

1. A method of inhibiting aging of skin using a stem cell conditioned medium, comprising:
    applying at least 10.0 wt. % of the stem cell conditioned medium to the skin of a subject in need thereof to inhibit oxidative stress and aging of the skin, wherein the stem cell conditioned medium scavenges free radicals and increases the survival rate of skin cells under oxidative stress; and wherein said stem cell conditioned medium is produced by: (a) culturing human Wharton's jelly mesenchymal stem cells in a cell culture dish containing a complete growth medium, wherein the complete growth medium includes α-MEM, fetal bovine serum, and human-basic fibroblast growth factors; and (b) sub-culturing the human Wharton's jelly mesenchymal stem cells in the complete growth medium at least three times and transferring the human Wharton's jelly mesenchymal stem cells to a basal medium to obtain said stem cell conditioned medium, wherein the basal medium includes α-MEM and human-basic fibroblast growth factors.

2. The method of claim 1, wherein the complete growth medium includes about 10 wt. %-20 wt. % of fetal bovine serum, about 2-6 ng/ml of human-basic fibroblast growth factors, and a remaining weight percentage of α-MEM, and the basal medium include about 2-6 ng/ml of human-basic fibroblast growth factors and a remaining weight percentage of α-MEM.

* * * * *